United States Patent [19]

Nielsen

[11] 4,203,870

[45] May 20, 1980

[54] CATALYST FOR HYDROGENATION OF GLYCOLIC ACID

[75] Inventor: Donald R. Nielsen, Corpus Christi, Tex.

[73] Assignee: PPG Industries, Inc., Pittsburgh, Pa.

[21] Appl. No.: 958,074

[22] Filed: Nov. 6, 1978

Related U.S. Application Data

[62] Division of Ser. No. 896,944, Apr. 17, 1978, Pat. No. 4,141,930.

[51] Int. Cl.$^2$ ............................................... B01J 29/10
[52] U.S. Cl. ...................................... 252/459; 252/472
[58] Field of Search ....................... 252/459, 454, 472; 568/864

[56] References Cited

U.S. PATENT DOCUMENTS

| | | | |
|---|---|---|---|
| 2,322,099 | 6/1943 | Schmidt | 568/864 |
| 2,472,832 | 6/1949 | Hunter et al. | 252/454 X |
| 2,607,805 | 8/1952 | Gresham | 568/864 |
| 2,666,756 | 1/1954 | Boyd et al. | 252/472 X |
| 2,793,241 | 5/1957 | Fawcett et al. | 252/472 X |
| 3,260,683 | 7/1966 | Endler | 252/473 |
| 3,352,913 | 11/1967 | Schmitt et al. | 252/472 X |
| 3,478,112 | 11/1969 | Adams et al. | 568/764 |
| 3,772,395 | 11/1973 | Yamaguchi et al. | 260/635 D |
| 3,848,003 | 11/1974 | Mesich et al. | 252/472 X |

*Primary Examiner*—Carl F. Dees
*Attorney, Agent, or Firm*—Edward J. Whitfield

[57] ABSTRACT

Glycolic acid is hydrogenated in the liquid phase in the presence of a catalyst consisting essentially of metallic cobalt and thorium oxide.

3 Claims, No Drawings

CATALYST FOR HYDROGENATION OF GLYCOLIC ACID

This is a division of application Ser. No. 896,944, filed Apr. 17, 1978, now U.S. Pat. No. 4,141,930.

BACKGROUND OF THE INVENTION

This invention relates to a catalyst particularly suited for use in catalyzing the liquid phase reduction of glycolic acid to ethylene glycol.

It is known to produce ethylene glycol by the liquid phase direct hydrogenation of glycolic acid in the presence of a catalyst as described, for example, in U.S. Pat. No. 2,607,805. It is also known to use metallic cobalt, either alone or in combination with various metal additives, as a hydrogenation catalyst as described, for example, in U.S. Pat. Nos. 2,322,099; 3,260,683; 3,478,112; 3,772,395; and 3,848,003.

Glycolic acid, however, tends to react with metallic cobalt to form cobalt glycolate. Although the cobalt glycolate may be reduced under typical hydrogenation reaction conditions with redeposition of cobalt metal, it has been observed that the catalytic activity of the redeposited cobalt metal is diminished resulting in decreased yields of and decreased selectivity to ethylene glycol.

In order to minimize the extent of reaction between metallic cobalt and glycolic acid, it is desirable to provide a cobalt-based catalyst that would enable conversion of glycolic acid to ethylene glycol in as short as possible a reaction time.

SUMMARY OF THE INVENTION

Ethylene glycol is prepared by hydrogenating glycolic acid in the liquid phase in the presence of a catalytically effective amount of a catalyst consisting essentially of metallic cobalt and thorium oxide.

DESCRIPTION OF THE INVENTION

In accordance with this invention, a combination of metallic cobalt and thorium oxide has been found to be particularly effective in catalyzing the liquid phase hydrogenation of glycolic acid to ethylene glycol. The catalyst of the invention, in addition to being highly selective to ethylene glycol, enables the production of ethylene glycol in high yields and in a shorter reaction time than cobalt alone or various other metal promoted cobalt catalysts under substantially the same reaction conditions.

The catalyst of the invention may be prepared by precipitating cobalt and thorium preferably as their oxalates or carbonates from an aqueous solution of cobalt and thorium salts. The precipitate is recovered from the solution, dried, pulverized, and heated in a hydrogen atmosphere to convert the cobalt oxalate or carbonate to metallic cobalt and the thorium oxalate or carbonate to thorium oxide. The thorium oxide content of the catalyst may vary from about 5 percent to about 20 percent by weight and preferably from about 10 percent to about 15 percent by weight thorium oxide with the balance metallic cobalt.

Any water soluble cobalt or thorium salts may be used to prepare the solution from which the cobalt and thorium are precipitated as their oxalates or carbonates, such as, for example, cobalt acetate, cobalt nitrate, cobalt chloride, cobalt sulfate, thorium nitrate, thorium chloride, thorium sulfate, or the like. The cobalt and thorium are precipitated as their oxalates or carbonates by the addition to the solution of oxalic acid, sodium carbonate, potassium carbonate, or the like.

Alternatively, other than precipitating the soluble cobalt and thorium salts as their oxalates or carbonates, substantially water insoluble thorium or cobalt compounds may be physically mixed in the dry state and reduced. If, however, insoluble cobalt or thorium compounds are used as starting materials, it is preferred that they first be slurried in water to assure intimate mixing. After slurrying, the solids are separated, dried, and reduced as described hereinabove. Some suitable, substantially nonwater soluble thorium and cobalt compounds are, for example, cobalt oxide, cobalt hydroxide, cobalt carbonate, cobalt oxalate, thorium oxalate, thorium oxide, thorium hydroxide, thorium carbonate, and the like.

The catalyst of the invention may be used with or without a support. If a continuous glycolic acid hydrogenation process is contemplated, it is preferred to use a supported catalyst whereas an unsupported catalyst is satisfactory for use in a batch process. The supported catalyst may be prepared by slurrying the support material along with and depositing the cobalt and thorium oxides, oxalates, carbonates or hydroxides on the support material and subjecting the same to a reducing atmosphere at an elevated temperature. Typically, the supported catalyst, after reduction, contains from about 10 percent to 80 percent, usually from about 40 percent to 60 percent, by weight of catalytic actives, i.e., metallic cobalt and thorium oxide, based on the total weight of catalytic actives and support material.

With regard to the choice of support material, those having high alkali metal, alkaline earth metal, or alumina contents have been found to be unsatisfactory since these tend to react with glycolic acid toform glycolates that are not readily reducible under ordinary liquid phase hydrogenation conditions. Consequently, silica or highly siliceous materials, i.e., those having a silica content of at least about 80 percent by weight, are preferred, such as, for example, kieselguhr or the like.

The liquid phase hydrogenation of glycolic acid using the catalyst of the invention may be conducted either batchwise or continuously.

In a typical batch reaction, a dilute, i.e., a 10 to 50 percent and usually about a 20 percent by weight, aqueous glycolic acid solution is charged along with the catalyst to an autoclave reactor provided with stirring means. The glycolic acid is contacted with elemental hydrogen at a temperature of from about 150° C. to about 220° C., preferably from about 180° C. to about 190° C. at a hydrogen pressure of from about 2,000 psig to about 10,000 psig, preferably from about 3,000 psig to about 5,000 psig. The reaction is continued with stirring until hydrogen uptake substantially ceases, usually from about 20 minutes to one hour. The catalyst is separated from the reaction mixture by, for example, filtration, and the ethylene glycol is recovered from the reaction mixture by conventional means, for example, fractional distillation.

In the batch hydrogenation of glycolic acid, sufficient catalyst is preferably used, whether supported or unsupported, to provide a molar ratio of metallic cobalt to glycolic acid of at least about 0.8. At a metallic cobalt to glycolic acid mole ratio of less than about 0.8, it has been observed that both the rate of conversion of glycolic acid and the yield of ethylene glycol are somewhat diminished. Although higher metallic cobalt to glycolic acid molar ratios may be used, no significant increase in either the rate of conversion of glycolic acid or ethylene glycol yield is observed at molar ratios in excess of about 1.3. Consequently, it is contemplated that in a batch hydrogenation the most beneficial results will obtain at metallic cobalt to glycolic acid molar ratios of from about 0.8 to about 1.3 with an apparent optimum at about 1.0 mole of metallic cobalt per mole of glycolic acid undergoing hydrogenation.

In a typical continuous hydrogenation process, aqueous glycolic acid solution and hydrogen gas are fed to a vertical reactor and passed through a bed of catalyst under substantially the same conditions of temperature and pressure at which the batch hydrogenation is conducted. When used in a continuous hydrogenation process, the catalyst is preferably carried on a support as described hereinabove and is preferably of a somewhat larger particle size, i.e., about 1 to 6 millimeters, than the relatively finely divided catalyst, i.e., about 100 to 400 mesh, typically used in the batch hydrogenation process.

In either the batch or continuous hydrogenation process, to further retard the tendency of the glycolic acid to react with the cobalt in the catalyst, it has been found to be advantageous to dilute the glycolic acid with both ethylene glycol and water rather than to use water alone as a diluent for the glycolic acid. A hydrogenation reaction mixture containing about 20 weight percent glycolic acid, about 70 weight percent ethylene glycol, and about 10 weight percent water has been found to be particularly efficacious and it is contemplated that beneficial results would obtain using hydrogenation reaction mixtures containing from about 10 to 40 weight percent glycolic acid, 5 to 20 weight percent water, and the balance ethylene glycol. It is also contemplated that ethylene glycol alone be used as a diluent for the glycolic acid. If a glycolic acid/ethylene glycol hydrogenation reaction mixture is used, the glycolic acid may, if desired, be esterified prior to reduction.

The invention is further illustrated but is not intended that it be limited by the following examples.

EXAMPLE 1

Preparation of Catalysts

A 1,000 milliliters of an aqueous containing 126 grams of ammonium dichromate $[(NH_4)_2Cr_2O_7]$ and 278 milliliters of 28 percent aqueous ammonium hydroxide solution were mixed with 1,000 milliliters of an aqueous solution containing 249 grams of cobaltous acetate $[Co(C_2H_3O_2)_2.4H_2O]$ at a temperature of 70° C. The resulting precipitate was recovered by suction filtration and dried to constant weight. 56 grams of the dried precipitate were ground to a powder and heated in a hydrogen gas stream at 530° C. to yield 35.1 grams of catalyst containing 54 weight percent metallic cobalt.

B. 70.5 grams cobaltous carbonate $[CoCO_3]$, 15.5 grams cupric acetate $[Cu(C_2H_3O_2)_2.H_2O]$, 22.5 grams manganous acetate $[Mn(C_2H_3O_2)_2.4H_2O]$, and 9.4 grams molybdic acid $[(NH_4)_6Mo_7O_{24}.4H_2O]$ were slurried with water, evaporated, and dried to constant weight. 22 grams of the dried material were ground to a powder and heated in a hydrogen gas stream at 400° C. to yield 17.1 grams of catalyst containing 66 weight percent metallic cobalt.

C. 1,000 milliliters of an aqueous solution of oxalic acid dihydrate were mixed with 1,000 milliliters of an aqueous solution containing 247 grams cobaltous acetate, 27.8 grams ferrous sulfate $[FeSO_4.7H_2O]$, 18.5 grams nickel formate dihydrate $[Ni(CHO_2)_2.2H_2O]$, and 20 grams cupric acetate at a temperature of 50° C. The resultant precipitate was recovered by suction filtration and dried to constant weight. 64.3 grams of the dried material were ground to a powder and heated in a hydrogen gas stream at 455° C. to yield 20.6 grams of catalyst containing 76 weight percent metallic cobalt.

D. 1,000 milliliters of an aqueous solution containing 148 grams cobaltous acetate, 32 grams cupric acetate, 11 grams manganous acetate, and 2.4 grams of 85 percent phosphoric acid were mixed with 1,000 milliliters of an aqueous solution containing 101 grams oxalic acid dihydrate at a temperature of 50° C. The resultant precipitate was recovered by suction filtration and dried to constant weight. 65.2 grams of the dried material were ground to a powder and heated in a hydrogen gas stream at 440° C. to yield 212 grams of catalyst containing 73 weight percent metallic cobalt.

E. 1,000 milliliters of an aqueous solution containing 249 grams cobaltous acetate, 18.5 grams nickel formate dihydrate, 10.1 grams cupric acetate, 5.0 grams ammonium dichromate, and 12.3 grams manganous acetate were mixed with 1,500 milliliters of an aqueous solution containing 202 grams ammonium bicarbonate. The resulting precipitate was recovered by suction filtration. 50 milliliters of an aqueous solution containing 5 grams ammonium molybdate and 5 grams polyphosphoric acid were thoroughly mixed with the wet filter cake and the cake was dried to constant weight. 38.2 grams of the dried solids were ground to a powder and heated in a hydrogen gas stream at 440° C. to yield 20.1 grams of catalyst containing 77 weight percent metallic cobalt.

F. 500 milliliters of an aqueous solution containing 125 grams cobaltous acetate were mixed with 500 milliliters of an aqueous solution containing 79 grams ammonium bicarbonate. The resulting precipitate was recovered by suction filtration and 50 milliliters of an aqueous solution containing 10.6 grams molybdic acid and 8.3 grams 28 percent ammonium hydroxide solution were thoroughly mixed with the wet filter cake. The cake was dried to constant weight and 30 grams of the dried material were ground to a powder and heated in a hydrogen gas stream at 400° C. to yield 17.3 grams of catalyst containing 91 weight percent metallic cobalt.

G. 600 milliliters of an aqueous solution containing 176 grams ammonium molybdate and 138 grams 28 percent ammonium hydroxide solution were mixed with 1,000 milliliters of an aqueous solution containing 249 grams cobaltous acetate. The resulting precipitate was recovered by suction filtration and dried to constant weight. 64.1 grams of the dried material were ground to a powder and heated in a hydrogen gas stream at 700° C. to yield 42.0 grams of catalyst containing 37 weight percent metallic cobalt.

H. 19.8 grams of powdered cobaltous oxide (CoO) prepared from cobaltous oxalate $(CoC_2O_4)$ which had been sintered at 1050° C. were heated in a hydrogen gas stream at 500° C. 14.9 grams of metallic cobalt was obtained which was mixed with 10 grams of CAL-SICAT®, a commercial catalyst composition containing about one weight percent platinum on carbon.

I. 30 grams of CELITE® 545 silica (Fisher Scientific Co. C-212) was added to 1,000 milliliters of an aqueous solution containing 125 grams cobaltous acetate. The solution was heated to 65° C. and mixed with 1,000 milliliters of an aqueous solution containing 103.6 grams potassium carbonate also heated to 65° C. The resulting precipitate was recovered by suction filtration and dried to constant weight. 42.3 grams of the dried material were ground to a powder and heated in a hydrogen gas stream at 400° C. to yield 29.4 grams of a supported catalyst containing 50 weight percent metallic cobalt.

J. 15 grams of CELITE® 545 was added to 150 milliliters of an aqueous solution containing 62 grams cobaltous acetate and evaporated to dryness under reduced pressure. The solids were mixed with 150 milliliters of an aqueous solution containing 35 grams oxalic acid dihydrate. The resultant precipitate was recovered by suction filtration and dried to constant weight. 57.1 grams of the dried material were ground to a powder and heated in a hydrogen gas stream at 400° C. to yield 27.4 grams of a supported catalyst containing 53 weight percent metallic cobalt.

K. 800 milliliters of an aqueous solution containing 164 grams cobaltous acetate, 4.9 grams thorium nitrate [$Th(NO_3)_4.4H_2O$], and 38 grams magnesium acetate [$Mg(C_2H_3O_2)_2.4H_2O$] were heated to 75° C. and mixed with 800 milliliters of an aqueous solution containing 111 grams of oxalic acid dihydrate. The resultant precipitate was recovered by suction filtration and dried to constant weight. 76.8 grams of the dried material were ground to a powder and heated in a hydrogen gas stream at 430° C. to yield 26.8 grams of catalyst containing 77 weight percent metallic cobalt.

L. 800 milliliters of an aqueous solution containing 164 grams cobaltous acetate and 9.8 grams thorium nitrate were heated to 55° C. and mixed with 800 milliliters of an aqueous solution containing 92 grams of oxalic acid dihydrate. The resultant precipitate was recovered by suction filtration and dried to constant weight. 69 grams of the dried material were ground to a powder and heated in a hydrogen gas stream at 430° C. to yield 22.9 grams of catalyst containing 87 weight percent metallic cobalt and 13 weight percent thorium oxide.

M. 19.5 grams of CELITE® 545 was added to 800 milliliters of an aqueous solution containing 96 grams cobaltous nitrate [$Co(NO_3)_2.6H_2O$] and 4.92 grams thorium nitrate to which was added 800 milliliters of an aqueous solution containing 53 grams potassium carbonate. The resulting precipitate was recovered by suction filtration and dried to constant weight. 46.5 grams of the dried material were ground to a powder and heated in a hydrogen gas stream at 430° C. to yield 32.7 grams of a supported catalyst containing 47 weight percent metallic cobalt, 5.7 weight percent thorium oxide, and the balance support material.

EXAMPLE 2

Hydrogenation of Glycolic Acid

A 300 cubic centimeter capacity stainless steel autoclave provided with stirring means (available from Autoclave Engineers, Inc.) was used as the hydrogenation reactor. For each hydrogenation run using each of the catalysts prepared in Example 1, the autoclave was charged under a nitrogen atmosphere with 0.262 moles glycolic acid as a 20 weight percent aqueous glycolic acid solution along with the respective catalyst. After charging with glycolic acid and catalyst, the autoclave was sealed and pressurized to 3,000 psig with nitrogen for 30 minutes to check for leaks and then swept with hydrogen. The autoclave was then brought up to operating temperature and pressurized with hydrogen gas to the desired operating pressure. Timing of the reaction was begun when hydrogen uptake was initially observed. The reaction was continued with stirring until cessation of hydrogen uptake was observed, after which the autoclave was cooled, vented, and disassembled. The catalyst was separated from the reaction products by suction filtration and the filtrate was submitted for analysis. The results and conditions of glycolic acid hydrogenation runs using catalysts A through M are summarized in Table I.

From an inspection of the data, it is seen that metallic cobalt alone (catalysts I and J) and certain of the catalysts containing metallic cobalt and metal additives (catalysts A and C) are effective in catalyzing the hydrogenation of glycolic acid. However, it is further seen that the catalyst of the invention (catalysts L and M) gives substantially equivalent results in significantly shorter reaction times and at lower temperatures. With regard to catalyst K, although this catalyst appeared to be very reactive, initially, hydrogen uptake ceased after 10 minutes. It is believed that the magnesium in the catalyst reacted with the glycolic acid to form a glycolate that was apparently unreducible under reaction conditions.

Although the invention has been described with specific references and specific details of embodiments thereof, it is to be understood that it is not intended to be so limited since changes and alterations therein may be made by those skilled in the art which are within the full intended scope of this invention as defined by the appended claims.

TABLE I

| Catalyst | Catalyst Composition | Moles Cobalt per Mole Glycolic Acid | Temp. °C. | Pressure, psig | Reaction Time, minutes | Ethylene Glycol, % Yield Of | Ethylene Glycol, % Selectivity To |
|---|---|---|---|---|---|---|---|
| A | Co + Cr | 1.20 | 225 | 3500–4100 | 139 | 92 | 96 |
| B | Co + Cu + Mn + Mo | 0.73 | 250 | 3800–4000 | 50 | 38 | 100 |
| C | Co + Fe + Ni + Cu | 1.02 | 234 | 3500–4100 | 49 | 95 | 96 |
| D | Co + Cu + Mn + P | 1.00 | 227 | 3500–4100 | 49 | 77 | 100 |
| E | Co + Ni + Cu + Mn + Cr | 1.00 | 244 | 3500–4100 | 142 | 85 | 86 |
| F | Co + Mo | 1.02 | 251 | 3600–4400 | 74 | 32 | 84 |
| G | Co + Mo | 1.01 | 245 | 3500–4100 | 58 | 45 | 64 |
| H | Co + Pt | 0.93 | 226 | 4200–4400 | 30 | 9 | 73 |
| I | Co | 0.96 | 226 | 3500–4100 | 66 | 96 | 93 |
| J | Co | 0.94 | 230 | 3500–4100 | 45 | 95 | 91 |
| K | Co + $ThO_2$ + MgO | 1.32 | 187 | 3000–3400 | 10 | 40 | 83 |
| L | Co + $ThO_2$ | 1.24 | 209 | 3500–4200 | 23 | 92 | 94 |
| M | Co + $ThO_2$ | 1.00 | 188 | 3500–4000 | 30 | 94 | 95 |

I claim:

1. A catalyst, especially suited for use in catalyzing the liquid phase hydrogenation of glycolic acid to produce ethylene glycol, consisting essentially of metallic cobalt and from about 5 to 20 percent by weight of thorium oxide based on the combined weights of metallic cobalt and thorium oxide.

2. The catalyst of claim 1 containing from about 10 to 15 percent by weight thorium oxide based on the combined weights of metallic cobalt and thorium oxide.

3. The catalyst of claim 1 carried on a particulate support containing at least about 80 percent silica.

* * * * *